United States Patent [19]
Grzegorzewski

[11] Patent Number: 5,494,639
[45] Date of Patent: Feb. 27, 1996

[54] BIOSENSOR FOR MEASURING CHANGES IN VISCOSITY AND/OR DENSITY OF A FLUID

[75] Inventor: Andrzej Grzegorzewski, Achim-Uphusen, Germany

[73] Assignee: Behringwerke Aktiengesellschaft, Marburg, Germany

[21] Appl. No.: 322,764

[22] Filed: Oct. 13, 1994

[30]  Foreign Application Priority Data

Oct. 13, 1993 [DE]  Germany .................... 43 34 834.3

[51] Int. Cl.⁶ .................................................. G01N 33/48
[52] U.S. Cl. .................... 422/82.01; 422/56; 436/501; 436/518
[58] Field of Search ................ 436/69, 63, 501, 436/518, 528, 529, 530; 422/56, 73, 58, 82.01; 73/64.1

[56]  References Cited

U.S. PATENT DOCUMENTS 4,236,893  12/1980  Rice .
4,314,821  2/1982  Rice .
4,735,906  4/1988  Bastiaans .

FOREIGN PATENT DOCUMENTS 0177858  3/1990  European Pat. Off. .
62-153761  12/1985  Japan .
74-4032767  5/1990  Japan .

*Primary Examiner*—James C. Housel
*Assistant Examiner*—Michael L. McGlashen
*Attorney, Agent, or Firm*—Spencer, Frank & Schneider

[57]  ABSTRACT

A disposable biosensor for measuring changes in viscosity and/or density in a test fluid includes a disposable housing surrounding a measuring chamber. A piezoelectric element is disposed in the measuring chamber and constitutes an oscillating unit. The piezoelectric element has a measuring surface adapted to be wetted with a measuring mixture comprising the test fluid and a reaction component. The reaction component is disposed inside the measuring chamber in a vicinity of and not touching the measuring surface of the piezoelectric element before any test fluid is introduced into the measuring chamber. Access is provided in the disposable housing for introducing the test fluid into the measuring chamber so that the test fluid comes into contact with the reaction component and the measuring surface of the piezoelectric element upon its introduction into the measuring chamber.

22 Claims, 3 Drawing Sheets

BIOSENSOR FOR MEASURING CHANGES IN VISCOSITY AND/OR DENSITY OF A FLUID

CROSS-REFERENCE TO RELATED APPLICATION

This application claims the priority of patent application No. P 43 34 834.3 filed Oct. 13, 1993 in Germany, the subject matter of which is incorporated herein by reference.

BACKGROUND OF THE INVENTION

The invention relates to a biosensor for measuring changes in viscosity or density in a test fluid, such as the coagulation of blood. The biosensor includes a housing surrounding a measuring chamber in which a piezoelectric element, and in particular a quartz crystal operating in a shear mode of vibration, is disposed. The piezoelectric element constitutes an oscillating unit with a measuring surface adapted to be wetted with a measuring mixture comprising the test fluid and a reaction component. Changes in the parameters of the oscillating are evaluated by a suitable electronic evaluation circuit.

European Patent EP-B 177 858, discloses a biosensor arrangement with which the coagulation rate of blood can be measured. A quartz crystal which is connected in the capacity of a resonant circuit to an oscillator having a fixed frequency is disposed in a measuring chamber which can be closed with a lid. The test fluid, which comprises the blood to be examined, is initially mixed with a coagulation component and applied to the measuring surface of the quartz crystal, upon which the coagulation rate of the blood is measured by evaluating a decrease in the vibration amplitude of the quartz crystal caused by a damping or mistuning of the resonant circuit by the coagulating blood. The elapsed time from the time the blood is mixed with the coagulation component up to the time of coagulation is measured by an electronic stopwatch. One disadvantage of the above arrangement is that, after a measurement has been made, the measuring chamber of the biosensor or the measuring surface of the quartz crystal can be cleaned only with great difficulty. Another disadvantage of this arrangement is that the elapsed time from the time the blood is mixed with the coagulation component until its application to the measuring surface must be carefully taken into account and monitored to avoid incorrect measurements. Yet another disadvantage of the above arrangement is the necessity for the relatively complicated procedure of initially mixing the blood with the coagulation component before applying it to the piezoelectric element. Similar devices are also disclosed in Japanese Patent Publications JP-A 62/153761 and JP-A 40/32767.

Biosensors for detecting antigen-antibody reactions which work with piezoelectric elements, for instance with a quartz crystal are also known. In such biosensors, an antigen-antibody is applied to the measuring surface of the piezoelectric element, upon which the piezoelectric element is dipped into the test fluid in order to measure and evaluate the resultant mistuning of the piezoelectric element as an oscillating circuit. Biosensors of this kind are described in U.S. Pat. Nos. 4,236,893 and 4,735,906. These biosensors have the disadvantage that the selectively absorbent layer of the oscillator surface must be cleaned before each new use, which procedure is very tedious and can gradually destroy the absorbent layer. Moreover, blood coagulation sensors of the above type in which the reaction component is initially applied to the measuring surface of the piezoelectric element would have the disadvantage that the piezoelectric element would be pre-strained by the reaction component, such that it would no longer be possible to make a measurement of the oscillating frequency of the piezoelectric element in the unstrained state.

SUMMARY OF THE INVENTION

It is an object of the present invention to provide a biosensor that is simple and hence economical in design for measuring changes in viscosity and/or density of a test fluid.

It is another object of the present invention to provide a biosensor which requires no initial addition of a reaction component to the test fluid.

It is yet another object of the present invention to provide a biosensor which presents no problems whatsoever involving cleaning of the biosensor after use.

The above objects are fulfilled in accordance with the invention by the provision of a disposable biosensor for measuring changes in at least one of viscosity and density in a test fluid, including: a disposable housing; a measuring chamber surrounded by the disposable housing; a piezoelectric element disposed in the measuring chamber and constituting an oscillating unit, the piezoelectric element having a measuring surface adapted to be wetted with a measuring mixture comprising the test fluid and a reaction component; means for disposing the reaction component inside the measuring chamber in a vicinity of and not touching the measuring surface of the piezoelectric element before any test fluid is introduced into the measuring chamber; and access means in said disposable housing for introducing the test fluid into the measuring chamber so that the test fluid comes into contact with the reaction component and the measuring surface of the piezoelectric element upon its introduction into the measuring chamber via the access.

In one form of the invention, the biosensor is sandwich-like, that is, it comprises a plurality of layers that are suitably glued together. Preferably, the housing comprises five layers, namely a first layer for forming a closed bottom for the housing, a second layer for leaving a free space under the piezoelectric element, a third layer for retaining the piezoelectric element, a fourth layer for forming the measuring chamber above the piezoelectric element, and a fifth layer for forming a lid for closing the measuring chamber above the piezoelectric element, the means for introducing the test fluid into the measuring chamber comprising an access disposed at the fifth layer for introducing the test fluid into the measuring chamber.

According to another form of the invention, the biosensor housing comprises two housing shells glued together, and the means for introducing the test fluid into the measuring chamber includes an access disposed at a first one of the two housing shells for introducing the test fluid into the measuring chamber, and a recess within which the piezoelectric element is disposed. In this form of the invention, a second one of the two housing shells forms a closed bottom for the housing and includes a protruding segment which rests on an edge of the piezoelectric element. A modified form of the above embodiment comprises a substrate part enclosed between the two housing shells on which the piezoelectric element is disposed.

In another form of the invention, the housing comprises a one-piece housing member including an inner chamber and an introduction conduit for inserting within the inner chamber a substrate carrying the reaction component and the piezoelectric element, the piezoelectric element being glued to the substrate.

In the above-described forms of the invention, the housing shells and the one-piece housing can be advantageously made of injection molded plastic.

The invention further provides a number of alternative embodiments for introducing the test fluid into the measuring chamber. According to one such embodiment, the access for introducing the test fluid comprises a bore communicating with the measuring chamber. According to another embodiment, the access comprises a membrane that covers the measuring chamber and which is permeable to the test fluid.

According to the present invention, the reaction component can be applied to the walls of the measuring chamber, or alternatively disposed on a substrate that is inserted into the measuring chamber in such a way that it does not touch the measuring surface. The substrate may preferably be an absorbent pad of batting or filter paper. It is also possible to use a grid of plastic or metal as the substrate. Moreover, instead of one reaction component, a plurality of different components can also be placed in the measuring chamber.

According to a modified form of the invention, a substrate board can be used which includes conductor tracks printed thereon, the conductor tracks having terminal faces adapted to extend out of the housing, and the piezoelectric element being mounted in the substrate board.

In the event that the biosensor is a blood coagulation sensor, the reaction component would comprise a substance for influencing the course of coagulation, such as $CaCl_2$. If the biosensor is used for detecting antigen-antibody reactions, then the reaction component would be an antigen or an antibody. To achieve especially stable measurements, the biosensor is preferably provided with a temperature equalization device in order to keep the temperature at a constant value.

According to another aspect of the invention, there is provided a biosensor system which includes a biosensor as previously discussed wherein an electronic evaluation circuit is coupled to the piezoelectric element for evaluating changes in parameters of the oscillating unit. In a preferred embodiment of the biosensor system, there is provided an oscillator circuit in which the piezoelectric element is connected for determining the frequency of the oscillator circuit. The electronic evaluation circuit comprises a microprocessor circuit coupled to the oscillator circuit for measuring and digitally evaluating changes in the frequency. In such a case, the microprocessor circuit can take the variable of time into account during its measurement function and perform a qualitative and/or quantitative evaluation of the parameters to be measured by means of suitable programming. The biosensor system of the present invention permits a measurement of the temperature present in the biosensor through an advantageous use of the temperature dependency of the piezoelectric element, thus allowing better control of the evaluation stage of the parameter(s) to be measured as a function of this temperature, or allowing temperature regulation of the biosensor to a constant temperature during this evaluation stage.

The biosensor of the present invention can be suitable for and adapted to all fluids, in other words liquids, viscous compositions, and gases. In addition to measuring blood coagulation and antigen-antibody reactions, measurements of changes in viscosity and/or density in other fields are also possible with the present invention.

BRIEF DESCRIPTION OF THE DRAWINGS

Further features and details of the present invention will become evident from the description below of embodiments thereof that are illustrated in the drawings, in which.

DETAILED DESCRIPTION OF THE PREFERRED EMBODIMENTS

Figure 1:
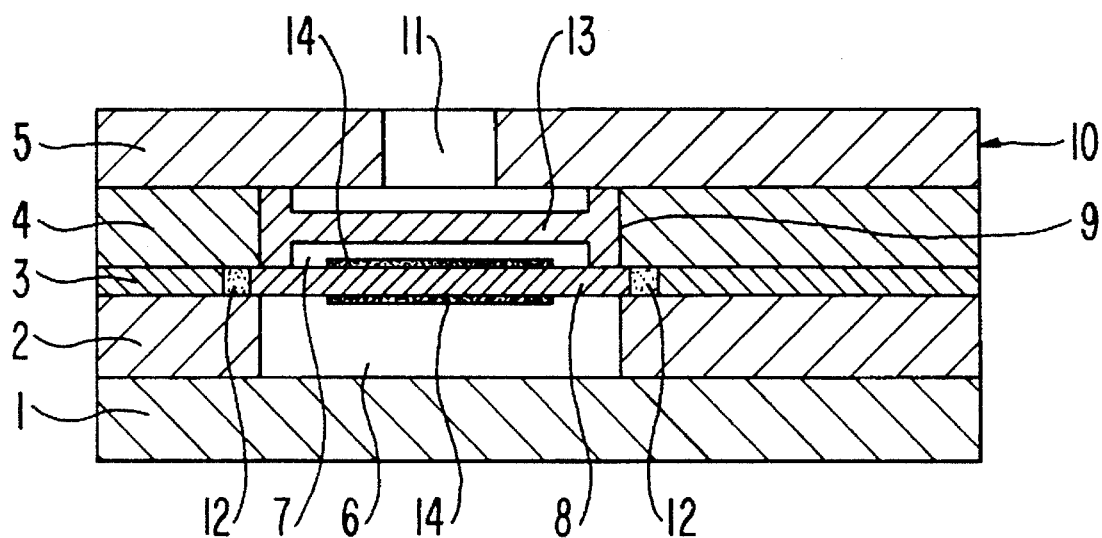
FIG. 1 is a cross section through a biosensor according to a first embodiment of the invention.

Referring to FIG. 1, the biosensor has a "sandwich-like" design including five layers. A first layer 1 forms the bottom of the biosensor 10. A second layer 2 includes a recess which creates a free space 6 under a piezoelectric element 8. A third layer 3 serves as a substrate for the piezoelectric element 8. A fourth layer has a recess 9 which forms a measuring chamber 7 above the piezoelectric element 8. And, finally, a fifth layer 5 forms a lid or cover for the measuring chamber 7 above the piezoelectric element 8. The fifth layer includes an access 11 in the form of a bore which makes it possible to introduce the test fluid into the measuring chamber 7. Instead of the cover layer 5 including bore 11, it is also possible to provide a membrane that is permeable to the test fluid.

Figure 2:
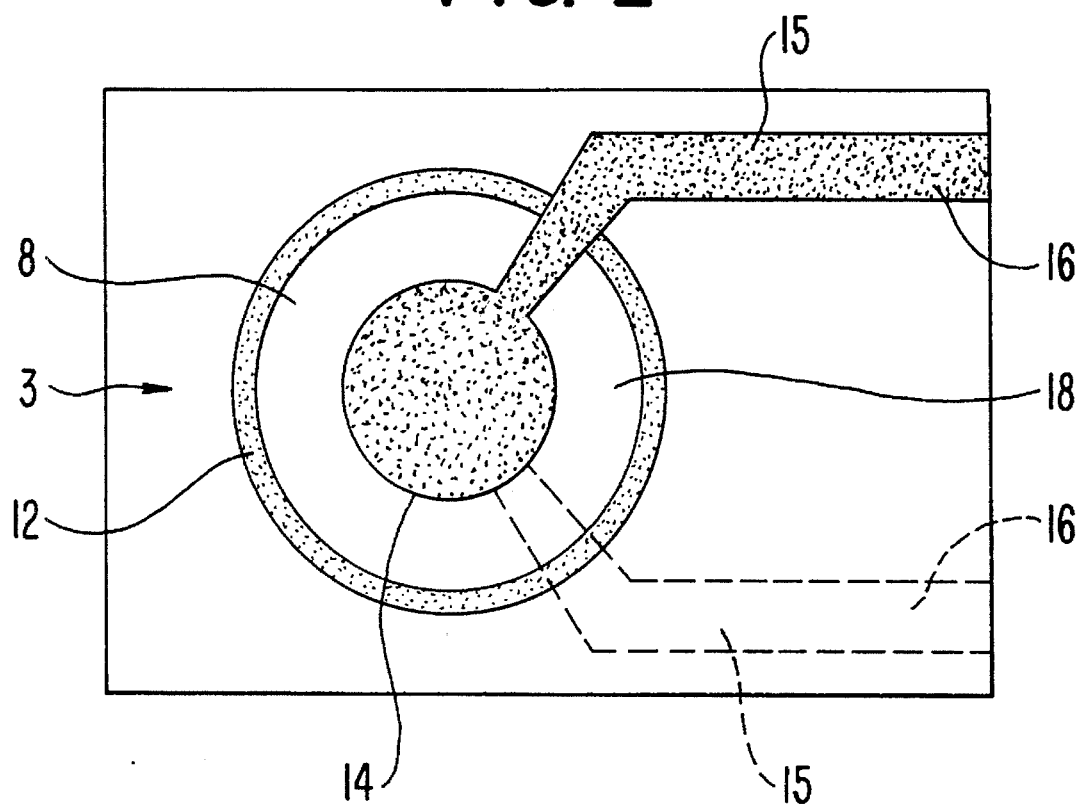
FIG. 2 is a plan view of a layer of the biosensor of FIG. 1 which carries the piezoelectric element.

Referring now to FIG. 2, the piezoelectric element 8 is disposed on a substrate board forming the third layer 3; specifically, the piezoelectric element 8 is glued into a suitable recess in the third layer 3 by means of an adhesive 12. Both faces of the piezoelectric element 8 are provided with electrodes 14, which communicate with terminal faces 16 that extend out of the housing, formed by the sandwiched layers, via conductor tracks 15 printed or otherwise applied to the third layer 3. The upper face (in terms of FIG. 1), which in FIG. 2 is identified by reference numeral 18, forms the measuring surface of the piezoelectric element 8.

A substrate 13 is inserted into the measuring chamber 7 (see FIG. 1) of the biosensor 10, or in other words into the recess 9, in such a way that it does not touch the measuring surface 18 of the piezoelectric element 8. The substrate 13 serves to receive a reaction component with which the test fluid is to react. When the test fluid is introduced via the access or bore 11, the fluid reacts with the reaction component located in a substrate 13 and reaches the measuring surface 18 of the piezoelectric element 8. Thus, because the onset of measurement of biosensor 10 can be defined exactly by the time of introduction of the fluid to be measured into bore 11, the usefulness of biosensor 10, contrary to biosensors of the prior art, is no longer a function of the skill of the technician in mixing the test fluid with a reaction component or in introducing the mixture into the biosensor.

Although in the present exemplary embodiments the reaction component is disposed in a substrate 13 that is inserted into the measuring chamber 7, it is also possible to apply the reaction component in a suitable way to the surfaces of the walls of the measuring chamber 7. However, care must be taken that the measuring surface 18 of the piezoelectric element 8 not be moistened during this process. It is also possible, instead of only one reaction component, to dispose a plurality of reaction components, for instance two such components, in the measuring chamber 7, for instance by means of a plurality of substrates 13, or on separate segments of the wall of the measuring chamber 7.

The sandwich-like biosensor 10 shown in FIGS. 1 and 2 can be produced in a suitable way, for instance by gluing together the individual layers 1–5. The individual layers 1–5 preferably comprise plastic films, although some of the layers may be made of paper. It is also possible to combine some of the layers 1–5, for instance, the layers 1 and 2, on the one hand, and 4 and 5, on the other hand. In this case, the recesses for the free space 6 and the measuring chamber 7 would be produced by an embossing process.

Figure 3:
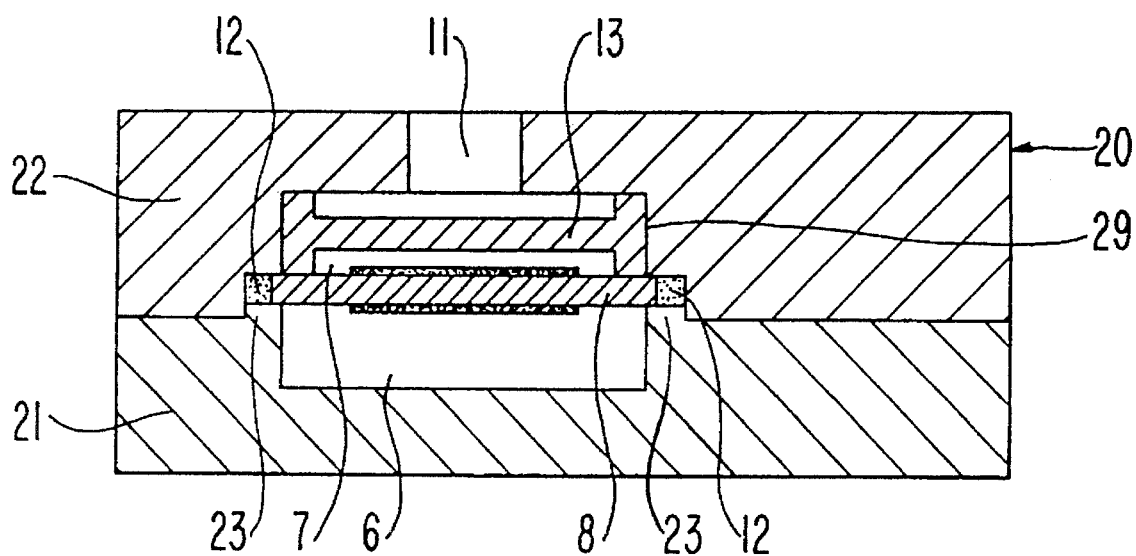
FIG. 3 is a cross section through a biosensor according to a second embodiment of the invention.

FIG. 3 shows an embodiment of a biosensor 20 in which the housing comprises two housing shells 21 and 22 that are glued together. The housing shell 21 forms a bottom layer for biosensor 20 and includes free space 6 under the piezoelectric element 8, while the housing shell 22 forms the top part of the biosensor and includes a recess 29 for the measuring chamber 7 and a bore 11 as the access to the measuring surface. The recess 29 in the upper housing shell 22 is formed such that it receives both the substrate 13 for the reaction component and the piezoelectric element 8, which is glued into the upper housing shell 22 by means of an adhesive 12. When the lower housing shell 21 is set in place, protruding segments 23 press against the outer region of the piezoelectric element 8 and fasten it to corresponding regions of the upper housing shell 22 as shown. It is thus apparent that biosensor 20 shown in FIG. 3 can be assembled in a simple manner.

Figure 4:
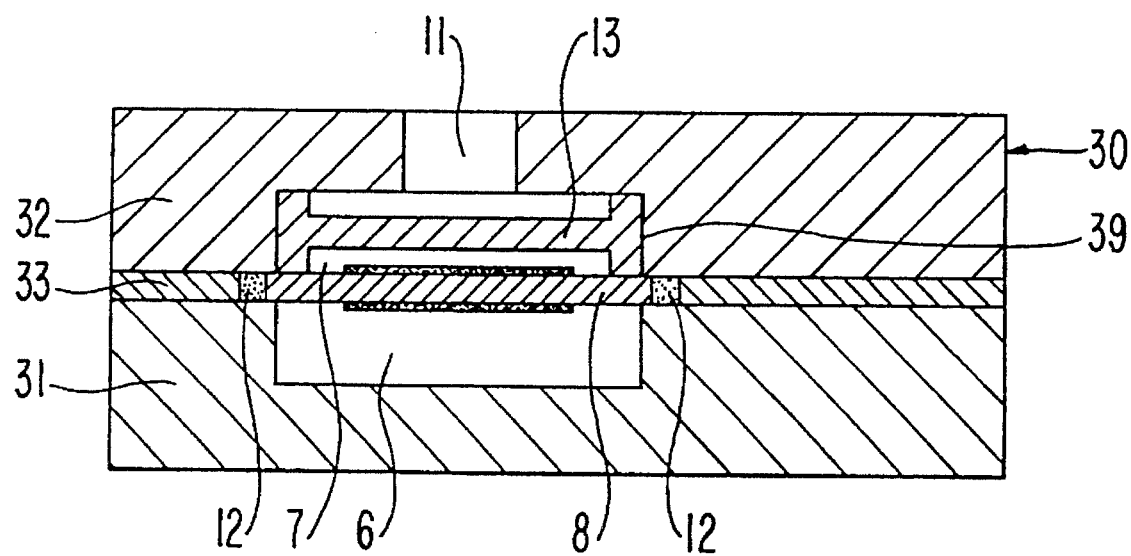
FIG. 4 is a cross section through a biosensor according to a third embodiment of the invention.

FIG. 4 shows another embodiment of the invention. Similarly to biosensor 20, biosensor 30 comprises a lower housing shell 31 and an upper housing shell 32 glued thereto. A substrate part 33 for the piezoelectric element 8 is enclosed between shells 31 and 32. Contrary to the embodiment of FIG. 3, the piezoelectric element 8 is not glued into the upper housing shell, but is instead mounted in a corresponding recess in the substrate part 13 by means of an adhesive 12. A recess 39 in the upper housing shell 32 retains only the substrate 13 for the reaction component and otherwise forms the measuring chamber 7.

Figure 5:
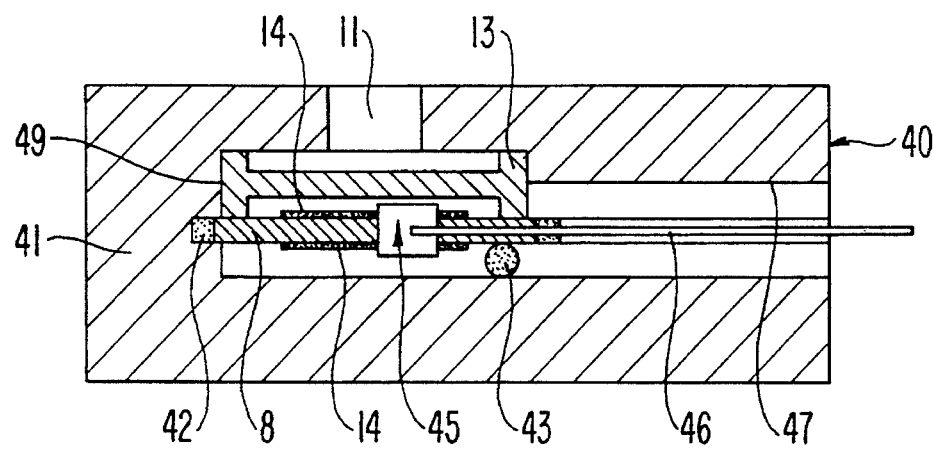
FIG. 5 is a cross section through a biosensor according to a fourth embodiment of the invention.

FIG. 5 shows a further embodiment of the invention in which biosensor 40 has an integral, or one-piece housing 41, which is provided with an inner chamber 49 and an introduction conduit 47. The chamber 49 is shaped such that both the substrate 13 for the reaction component and a contact clamp 45 holding the piezoelectric element 8 can be received and securely mounted into housing 41. Moreover access 11 provides a suitable opening to the outside through which the test fluid can be introduced.

The piezoelectric element 8 with the contact clamp 45 is secured in the interior of the housing 41 by adhesive components 42 and 43 after being inserted through the introduction conduit 47. The electrodes 14 of the piezoelectric element 8 are extended outward via connection wires 46.

The housing shells of the three embodiments shown in FIGS. 3, 4 and 5, respectively, are preferably made from a suitable plastic by an injection molding process. Because production of the above-described embodiments is very simple and economical, biosensors 10, 20, 30, and 40 can be disposable, which has the advantage that the biosensors can be pre-assembled and delivered already provided with the reaction component therein. Subsequent use of an already used biosensor of the present invention would, however, not be recommended in view of the employed design.

Figure 6:
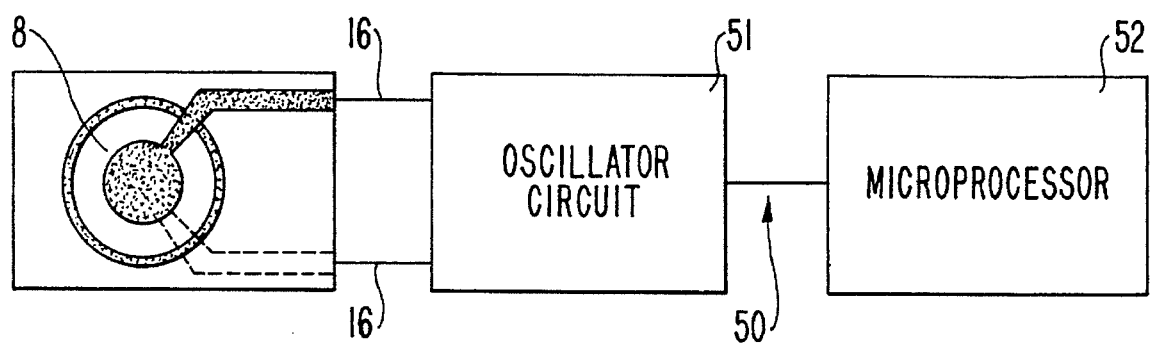
FIG. 6 is a block circuit diagram of a biosensor system with the novel biosensor of the invention.

Referring now to FIG. 6, there is shown a biosensor system which includes a circuit 50 comprised of an oscillator circuit 51, a microprocessor circuit 52, and a biosensor according to the present invention whose piezoelectric element 8 communicates with the oscillator circuit 51 via terminal faces 16. Oscillator circuit 51 uses piezoelectric element 8, which preferably comprises a quartz crystal, as a frequency-determining element. Microprocessor circuit 52 in turn includes a corresponding frequency measuring routine for measuring the oscillation frequency of oscillator 51. Microprocessor 52 can be configured and programmed to evaluate frequency changes or other related parameters of the piezoelectric element 8 or oscillator circuit 51 and in so doing to take the time component of these evaluations into account. By suitable programming of the microprocessors, a suitable evaluation can be can be effected of the measured values and displayed on a screen or other output unit (not shown).

While a preferred embodiment of the invention has been described and illustrated, it should be recognized that numerous modifications and variations of the disclosed embodiment may be made without departing from the scope of the invention as defined in the appended claims which therefore should not be limited to the details disclosed herein, but rather should be interpreted to embrace any and all equivalent apparatus.

What is claimed is:

1. A disposable biosensor for measuring changes in at least one of viscosity and density in a test fluid, including:

a disposable housing;

a measuring chamber surrounded by the disposable housing;

a piezoelectric element disposed in the measuring chamber and constituting an oscillating unit, the piezoelectric element having a measuring surface adapted to be wetted with a measuring mixture comprising the test fluid and a reaction component;

means for disposing the reaction component inside the measuring chamber in a vicinity of and not touching the measuring surface of the piezoelectric element before any test fluid is introduced into the measuring chamber; and access means in said disposable housing for introducing the test fluid into the measuring chamber so that the test fluid comes into contact with the reaction component and the measuring surface of the piezoelectric element upon its introduction into the measuring chamber.

2. The biosensor according to claim 1, wherein the piezoelectric element is a quartz crystal operational in a shear mode of vibration.

3. The biosensor according to claim 1, wherein the disposable housing comprises a plurality of layers glued to one another.

4. The biosensor of claim 3, wherein the plurality of layers comprises five layers, including:

a first layer forming a closed bottom for the housing;

a second layer disposed above the first layer and leaving a free space under the piezoelectric element;

a third layer disposed above the second layer and retaining the piezoelectric element;

a fourth layer disposed above the third layer and forming the measuring chamber above the piezoelectric element; and a fifth layer disposed above the fourth layer and forming a lid for closing the measuring chamber above the piezoelectric element, the access means being disposed in the fifth layer for introducing the test fluid into the measuring chamber.

5. The biosensor according to claim 1, wherein the housing comprises two housing shells glued together and the piezoelectric element is inserted between the two housing shells.

6. The biosensor of claim 5, wherein a first one of the housing shells includes the access means and a recess for receiving the piezoelectric element, and a second one of the two housing shells forms a closed bottom for the housing and includes a protruding segment which rests on an edge of the piezoelectric element.

7. The biosensor of claim 1, wherein the disposing means comprises a substrate carrying the reaction component and the disposable housing comprises a one-piece housing member including an inner chamber and an introduction conduit communicating with the inner chamber, the substrate and the piezoelectric element being inserted into the inner chamber through the introduction conduit, the piezoelectric element being glued to the substrate.

8. The biosensor according to claim 1, wherein the housing is made of injection molded plastic.

9. The biosensor according to claim 1, wherein the access means comprises a bore communicating with the measuring chamber.

10. The biosensor according to claim 1, wherein the access means comprises a membrane covering the measuring chamber and permeable to the test fluid.

11. The biosensor according to claim 1, wherein the measuring chamber has walls to which the reaction component is applied, said walls with the reaction component constituting the disposing means.

12. The biosensor according to claim 1, wherein said disposing means includes a substrate containing the reaction component and adapted to be inserted into the measuring chamber such that it does not touch the measuring surface.

13. The biosensor according to claim 12, wherein the substrate comprises an absorbent pad of one of batting and filter paper.

14. The biosensor according to claim 12, wherein the substrate comprises a grid of one of plastic and metal.

15. The biosensor according to claim 1, wherein the housing includes a substrate board having conductor tracks printed thereon and terminal faces extending out of the housing, the piezoelectric element is mounted on the substrate board and is connected to the terminal faces by way of the conductor tracks.

16. The biosensor according to claim 1, wherein the biosensor is a blood coagulation sensor, and wherein the reaction component comprises a substance for influencing blood coagulation.

17. The biosensor according to claim 16, wherein the substance comprises $CaCl_2$.

18. The biosensor according to claim 1, wherein the biosensor is a sensor for detecting antigen-antibody reactions, and wherein the reaction component comprises one of an antigen and an antibody.

19. The biosensor according to claim 1, and further including a temperature equalization device for keeping temperature of the biosensor at a constant value.

20. A biosensor system including the biosensor according to claim 1 and further including an electronic evaluation circuit coupled to said piezoelectric element for evaluating changes in parameters of the oscillating unit.

21. The biosensor system according to claim 20, wherein the electronic evaluation circuit comprises an oscillator circuit in which the piezoelectric element is connected for determining frequency of the oscillator circuit and a microprocessor circuit coupled to the oscillator circuit for measuring and digitally evaluating changes in the frequency.

22. The biosensor system according to claim 20, wherein the piezoelectric element has a temperature dependency and said electronic evaluation circuit measures temperature of the biosensor element utilizing the temperature dependency of the piezoelectric element.

\* \* \* \* \*